United States Patent
Desenne et al.

(10) Patent No.: US 7,223,294 B2
(45) Date of Patent: *May 29, 2007

(54) COMPOSITION FOR THE OXIDATION DYEING OF KERATIN FIBRES, COMPRISING A POLYOXYALKYLENATED CARBOXYLIC ACID ETHER, AN ASSOCIATIVE POLYMER AND AN UNSATURATED FATTY ALCOHOL

(75) Inventors: Patricia Desenne, Bois Colombres (FR); Cecile Bebot, Clichy (FR); Florence Laurent, Bois Colombres (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/323,770

(22) Filed: Dec. 20, 2002

(65) Prior Publication Data

US 2003/0192134 A1 Oct. 16, 2003

(30) Foreign Application Priority Data

Dec. 21, 2001 (FR) .................................. 01 16740

(51) Int. Cl.
*A61K 7/13* (2006.01)
(52) U.S. Cl. ...................... 8/405; 8/406; 8/410; 8/421; 8/429; 8/512; 8/554; 8/582; 8/611
(58) Field of Classification Search ............... 8/405, 8/406, 410, 421, 429, 512, 554, 582, 611
See application file for complete search history.

(56) References Cited

U.S. PATENT DOCUMENTS

| 4,774,075 | A | 9/1988 | Lang et al. ................ 424/47 |
| 6,254,647 | B1 | 7/2001 | Frohling ..................... 8/406 |
| 6,261,325 | B1 | 7/2001 | de la Mettrie et al. ......... 8/405 |
| 6,436,151 | B2 * | 8/2002 | Cottard et al. ................ 8/406 |
| 6,800,098 | B1 | 10/2004 | Allard et al. ................. 8/405 |
| 2001/0023514 | A1 * | 9/2001 | Cottard et al. ................ 8/406 |
| 2001/0023515 | A1 * | 9/2001 | Cottard et al. ................ 8/406 |

FOREIGN PATENT DOCUMENTS

| DE | 196 13 567 | 10/1997 |
| DE | 199 59 320 | 6/2001 |
| EP | 0 943 320 | 9/1999 |
| WO | 01/41723 | 6/2001 |

OTHER PUBLICATIONS

Database Chemical Abstract, AN 135:200152, JP 2001-233748, Aug. 28, 2001.
Research Disclosure, vol. 439, p. 1935, "Improvement of Dye Uptake by Introduction of Emollients in Hair Colouring Products", Nov. 2000.

* cited by examiner

*Primary Examiner*—Eisa Elhlio
(74) *Attorney, Agent, or Firm*—Oblon, Spivak, McClelland, Maier & Neustadt, P.C.

(57) ABSTRACT

The invention relates to a composition for the oxidation dyeing of keratin fibres, in particular of human keratin fibres and more particularly the hair, containing, in a medium that is suitable for dyeing, at least one oxidation dye, wherein it also contains at least one polyoxyalkylenated carboxylic acid ether or a salt thereof, at least one associative polymer and at least one fatty alcohol ($C_8$–$C_{30}$) comprising at least one unsaturation.

The invention also relates to the dyeing devices and processes using the said composition.

41 Claims, No Drawings

COMPOSITION FOR THE OXIDATION DYEING OF KERATIN FIBRES, COMPRISING A POLYOXYALKYLENATED CARBOXYLIC ACID ETHER, AN ASSOCIATIVE POLYMER AND AN UNSATURATED FATTY ALCOHOL

FIELD OF THE INVENTION

The present invention relates to a composition useful for the oxidation dyeing of keratin fibres, in particular of human keratin fibres and more particularly the hair, comprising, preferably in a medium that is suitable for dyeing, at least one oxidation dye, and also at least one polyoxyalkylenated carboxylic acid ether or a salt thereof, at least one associative polymer and at least one fatty alcohol ($C_8$–$C_{30}$) comprising at least one unsaturation.

The invention also relates to the dyeing devices and processes using the composition.

BACKGROUND OF THE INVENTION

It is known practice to dye keratin fibres, and in particular human hair, with dye compositions containing oxidation dye precursors, generally known as "oxidation bases", in particular ortho- or para-phenylenediamines, ortho- or para-aminophenols, and heterocyclic bases.

Oxidation dye precursors are compounds that are initially uncoloured or only weakly coloured, which develop their dyeing power on the hair in the presence of oxidizing agents, leading to the formation of coloured compounds. The formation of these coloured compounds results either from an oxidative condensation of the "oxidation bases" with themselves or from an oxidative condensation of the "oxidation bases" with coloration modifiers, or "couplers", which are generally present in the dye compositions used in oxidation dyeing and are represented more particularly by meta-phenylenediamines, meta-aminophenols and meta-diphenols, and certain heterocyclic compounds.

The variety of molecules used, which consist on the one hand of the "oxidation bases" and on the other hand of the "couplers", allows a very wide range of colours to be obtained.

These oxidation bases and couplers are formulated in vehicles or supports allowing them to be applied to keratin fibres after mixing with an oxidizing agent.

These vehicles are generally aqueous and usually comprise one or more surfactants.

Thus, it has already been recommended to use anionic surfactants, in combination with associative polymers and saturated fatty alcohols. The said combinations produce oxidation dye compositions that generate shades with very good dyeing properties. However, the search continues for supports that can further improve the properties of the colorations obtained.

SUMMARY OF THE INVENTION

Thus, after considerable research conducted in this matter, the inventors have now discovered that it is possible to obtain oxidation dye compositions that produce even more powerful and more chromatic shades, by introducing into the dye composition at least one polyoxyalkylenated carboxylic acid ether or a salt thereof, at least one associative polymer and at least one fatty alcohol ($C_8$–$C_{30}$) comprising at least one unsaturation.

DETAILED DESCRIPTION OF THE INVENTION

One subject of the present invention is thus a composition useful for the oxidation dyeing of keratin fibres, in particular of human keratin fibres and more particularly the hair, comprising, preferably in a medium that is suitable for dyeing, at least one oxidation dye, and wherein it also comprises at least one polyoxyalkylenated carboxylic acid ether or a salt thereof, at least one associative polymer and at least one fatty alcohol ($C_8$–$C_{30}$) comprising at least one unsaturation.

The said dye composition also makes it possible to give a more transparent appearance to the formulations which comprise it and which are liquid.

The shades obtained moreover have good fastness.

Another subject of the invention relates to a ready-to-use composition useful for the oxidation dyeing of keratin fibres, which comprises, preferably in a medium that is suitable for dyeing, at least one composition as described above and at least one oxidizing agent.

For the purposes of the present invention, the expression "ready-to-use composition" means the composition intended to be applied immediately to the keratin fibres, i.e. it may be stored before use without further modification, or may result from the extemporaneous mixing of two or more compositions.

The invention is also directed towards a process for the oxidation dyeing of keratin fibres, and in particular of human keratin fibres such as the hair, which consists in applying to the fibres a dye composition comprising, in a medium that is suitable for dyeing, at least one oxidation dye, the colour being developed at alkaline, neutral or acidic pH using an oxidizing composition comprising, in a medium that is suitable for dyeing, at least one oxidizing agent, which is mixed with the dye composition just at the time of use, or which is applied sequentially without intermediate rinsing, the dye composition and the oxidizing composition also comprising, distributed indifferently between the two, at least one polyoxyalkylenated carboxylic acid ether or a salt thereof, at least one associative polymer and at least one fatty alcohol ($C_8$–$C_{30}$) comprising at least one unsaturation.

In one variant of the said process, the polyoxyalkylenated carboxylic acid ether(s) or salts thereof, associative polymer(s) and fatty alcohol(s) ($C_8$–$C_{30}$) comprising at least one unsaturation are combined in the same dye composition or oxidizing composition and even more particularly in the dye composition.

A subject of the invention is also a multi-compartment dyeing device or "kit" for the oxidation dyeing of keratin fibres, in particular of human keratin fibres and more particularly the hair, which comprises a compartment containing a dye composition comprising, in a medium that is suitable for dyeing, at least one oxidation dye, and another compartment containing an oxidizing composition comprising, in a medium that is suitable for dyeing, an oxidizing agent, the dye composition and the oxidizing composition also comprising, distributed indifferently between the two, at least one polyoxyalkylenated carboxylic acid ether or a salt thereof, at least one associative polymer and at least one fatty alcohol ($C_8$–$C_{30}$) comprising at least one unsaturation.

In one device variant, the polyoxyalkylenated carboxylic acid ether(s) or salts thereof, associative polymer(s) and fatty alcohol(s) ($C_8$–$C_{30}$) comprising at least one unsaturation are combined in the same dye composition or oxidizing composition, and even more particularly in the dye composition.

However, other characteristics, aspects, subjects and advantages of the invention will emerge even more clearly on reading the description and the examples that follow.

Oxyalkylenated Carboxylic Acid Ethers and Salts Thereof

The expression "oxyalkylenated carboxylic acid ether and salt thereof" preferably means any compound of formula (I) below:

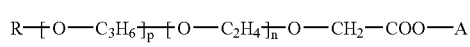

(I)

in which:

R represents a linear or branched $C_8$–$C_{22}$ alkyl or alkenyl radical or mixture of radicals, a ($C_8$–$C_9$)alkylphenyl radical or a radical R'CONH—CH$_2$—CH$_2$— with R' denoting a linear or branched $C_{11}$–$C_{21}$ alkyl or alkenyl radical, n is an integer or fraction ranging from 2 to 24, p is an integer or fraction ranging from 0 to 6, A denotes a hydrogen atom or Na, K, Li, 1/2Mg or a monoethanolamine, ammonium or triethanolamine residue.

The polyoxyalkylenated carboxylic acid ethers and salts thereof preferably used according to the present invention are selected from the group consisting of those of formula (I) in which R denotes a ($C_{12}$–$C_{14}$)alkyl, oleyl, cetyl or stearyl radical or mixture of radicals; a nonylphenyl or octylphenyl radical, A denotes a hydrogen or sodium atom, p=0, and n ranges from 2 to 20 and preferably from 2 to 10.

Compounds of formula (I) in which R denotes a ($C_{12}$) alkyl radical, A denotes a hydrogen or sodium atom, p=0 and n ranges from 2 to 10 are even more preferably used.

Among the commercial products that may preferably be used are the products sold by the company Chem Y under the names:

Akypo® NP 70 (R=nonylphenyl, n=7, p=0, A=H)
Akypo® NP 40 (R=nonylphenyl, n=4, p=0, A=H)
Akypo® OP 40 (R=octylphenyl, n=4, p=0, A=H)
Akypo® OP 80 (R=octylphenyl, n=8, p=0, A=H)
Akypo® OP 190 (R=octylphenyl, n=19, p=0, A=H)
Akypo® RLM 38 (R=($C_{12}$—$C_{14}$)alkyl, n=3.8, p=0, A=H)
Akypo® RLM 38 NV (R=($C_{12}$–$C_{14}$)alkyl, n=4, p=0, A=Na)
Akypo® RLM 45 (R=($C_{12}$–$C_{14}$)alkyl, n=4.5, p=0, A=H)
Akypo® RLM 45 NV (R=($C_{12}$–$C_{14}$)alkyl, n=4.5, p=0, A=Na)
Akypo® RLM 100 (R=($C_{12}$–$C_{14}$)alkyl, n=10, p=0, A=H)
Akypo® RLM 100 NV (R=($C_{12}$–$C_{14}$)alkyl, n=10, p=0, A=Na)
Akypo® RLM 130 (R=($C_{12}$–$C_{14}$)alkyl, n=13, p=0, A=H)
Akypo® RLM 160 NV (R=($C_{12}$–$C_{14}$)alkyl, n=16, p=0, A=Na)
Akypo® RO 20 (R=oleyl, n=2, p=0, A=H)
Akypo® RO 90 (R=oleyl, n=9, p=0, A=H)
Akypo® RCS 60 (R=cetyl/stearyl, n=6, p=0, A=H)
Akypo® RS 60 (R=stearyl, n=6, p=0, A=H)
Akypo® RS 100 (R=stearyl, n=10, p=0, A=H)
Akypo® RO 50 (R=oleyl, n=5, p=0, A=H),
or by the company Sandoz under the names:
Sandopan ACA-48 (R=cetyl/stearyl, n=24, p=0, A=H)
Sandopan DTC-Acid (R=($C_{13}$)alkyl, n=6, p=0, A=H)
Sandopan DTC (R=($C_{13}$)alkyl, n=6, p=0, A=Na)
Sandopan LS 24 (R=($C_{12}$–$C_{14}$)alkyl, n=12, p=0, A=Na)
Sandopan JA 36 (R=($C_{13}$)alkyl, n=18, p=0, A=H),
and more particularly the products sold under the following names:

Akypo® NP 70
Akypo® NP 40
Akypo® OP 40
Akypo® OP 80
Akypo® RLM 25
Akypo® RLM 45
Akypo® RLM 100
Akypo® RO 20
Akypo® RO 50
Akypo® RLM 38.

The polyoxyalkylenated carboxylic acid ethers or salts thereof preferably represent from about 2% to 15% and more preferably from about 3% to 10% of the total weight of the dye composition, and from about 0.5% to 15% and more preferably from about 0.7% to 10% of the total weight of the ready-to-use dye composition (comprising the oxidizing agent).

Associative Polymers that May Be used According to the Invention

Associative polymers are water-soluble polymers capable, in an aqueous medium, of reversibly associating together or with other molecules.

Their chemical structure comprises hydrophilic zones and hydrophobic zones characterized by at least one fatty chain.

The associative polymers according to the invention may be of anionic, cationic or amphoteric type, and preferably of nonionic type.

Their weight concentration in the dye composition can preferably range from about 0.01% to 10% of the total weight of the composition, and in the ready-to-use composition (comprising the oxidizing agent), from about 0.0025% to 10% of the total weight of the composition. More preferably, this amount ranges from about 0.1% to 5% by weight in the dye composition and from about 0.025% to 10% in the ready-to-use composition.

Associative Polymers of Anionic Type:

Among these, mention may be made of:

(I) those comprising at least one hydrophilic unit and at least one fatty-chain allyl ether unit, more particularly those whose hydrophilic unit consists of an ethylenic unsaturated anionic monomer, more particularly a vinylcarboxylic acid and most particularly an acrylic acid or a methacrylic acid or mixtures thereof, the fatty-chain allyl ether unit of which corresponding to the monomer of formula (I) below:

(I)

in which R' denotes H or CH$_3$, B denotes an ethyleneoxy radical, n is zero or denotes an integer ranging from 1 to 100, R denotes a hydrocarbon-based radical selected from the group consisting of alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of $(C_{10}-C_{30})$alkyl ester of unsaturated carboxylic acid type.

Preferably, these polymers are selected from the group consisting of those in which the hydrophilic unit of unsaturated olefinic carboxylic acid type corresponds to the monomer of formula (II) below:

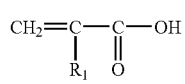
(II)

in which $R_1$ denotes H or $CH_3$ or $C_2H_5$, that is to say acrylic acid, methacrylic acid or ethacrylic acid units, and in which the hydrophobic unit of $(C_{10}-C_{30})$alkyl ester of unsaturated carboxylic acid type corresponds to the monomer of formula (III) below:

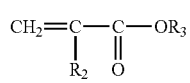
(III)

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}-C_{30}$ and preferably $C_{12}-C_{22}$ alkyl radical.

$(C_{10}-C_{30})$ alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture comprising:

(i) essentially acrylic acid, (ii) an ester of formula (III) described above in which $R_2$ denotes H or $CH_3$, $R_3$ denoting an alkyl radical containing from 12 to 22 carbon atoms, (iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}-C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}-C_{30}$ alkyl acrylate (hydrophobic unit) and 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}-C_{38}$ α-olefin/alkyl maleate terpolymers, such as the product (maleic anhydride/$C_{30}-C_{38}$ α-olefin/isopropyl maleate copolymer) sold under the name Performa V 1608® by the company Newphase Technologies.

(IV) acrylic terpolymers comprising:

(a) about 20% to 70% by weight of a carboxylic acid containing α,β-monoethylenic unsaturation, (b) about 20% to 80% by weight of a non-surfactant monomer containing α,β-monoethylenic unsaturation other than (a), (c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1-C_4$ alcohol.

An example of a compound of this type which may be mentioned is Aculyn 22® sold by the company Rohm & Haas, which is a methacrylic acid/ethyl acrylate/stearyl methacrylate oxyalkylenated terpolymer.

Associative Polymers of Cationic Type

Among these, mention may be made of:

(I) the cationic associative polyurethanes whose family has been described by the Applicant in French patent application No. 0 009 609; they may be represented by the general formula (Ia) below:

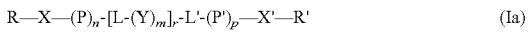
(Ia)

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25, n, m and p each range, independently of each other, from 0 to 1000;

the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (Ia) described above and in which:

R and R' both independently represent a hydrophobic group,

X and X' each represent a group L", n and p are between 1 and 1000, and

L, L', L", P, P', Y and m have the meaning given above.

Another preferred family of cationic associative polyurethanes is the one corresponding to formula (Ia) above in which:

R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulphate, etc.

Yet another preferred family of cationic associative polyurethanes is the one corresponding to formula (Ia) above in which:

R and R' both independently represent a hydrophobic group,

X and X' both independently represent a group comprising a quaternary amine, n and p are 0, and L, L', Y and m have the meaning given above.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote(s) a group comprising a tertiary or quaternary amine, X and/or X' may represent one of the following formulae:

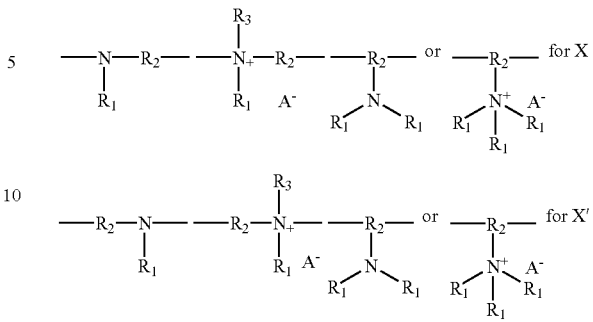

in which:

$R_2$ represents a linear or branched alkylene radical containing from 1 to 20 carbon atoms, optionally comprising a saturated or unsaturated ring, or an arylene radical, one or more of the carbon atoms possibly being replaced with a hetero atom selected from the group consisting of N, S, O and P;

$R_1$ and $R_3$, which may be identical or different, denote a linear or branched $C_1$–$C_{30}$ alkyl or alkenyl radical or an aryl radical, at least one of the carbon atoms possibly being replaced with a hetero atom selected from the group consisting of N, S, O and P;

$A^-$ is a physiologically acceptable counter-ion.

The groups L, L' and L" represent a group of formula:

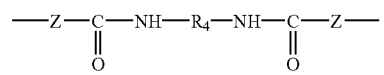

in which:

Z represents —O—, —S— or —NH—; and $R_4$ represents a linear or branched alkylene radical containing from 1 to 20 carbon atoms, optionally comprising a saturated or unsaturated ring or an arylene radical, one or more of the carbon atoms possibly being replaced with a hetero atom selected from the group consisting of N, S, O and P.

The groups P and P' comprising an amine function may represent at least one of the following formulae:

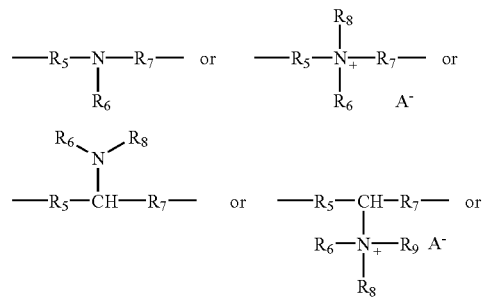

-continued

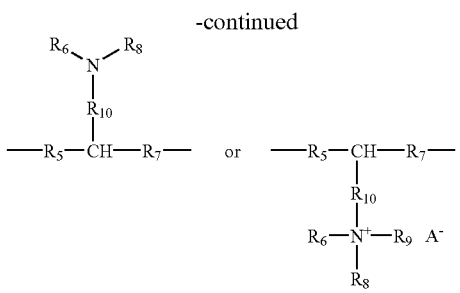

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group which may contain one or more hetero atoms selected from the group consisting of N, O, S and P, and $A^-$ is a physiologically acceptable counter-ion.

As regards the meaning of Y, the term "hydrophilic group" means a polymeric or non-polymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulphonated polyesters, sulphonated polyamides or a mixture of these polymers. The hydrophilic compound is preferentially a polyether and in particular a poly(ethylene oxide) or poly(propylene oxide).

The cationic associative polyurethanes of formula (Ia) according to the invention are formed from diisocyanates and from various compounds with functions containing labile hydrogen. The functions containing labile hydrogen may be alcohol, primary or secondary amine or thiol functions giving, after reaction with the diisocyanate functions, polyurethanes, polyureas and polythioureas, respectively. The term "polyurethanes" in the present invention encompasses these three types of polymer, namely polyurethanes per se, polyureas and polythioureas, and also copolymers thereof.

A first type of compound involved in the preparation of the polyurethane of formula (Ia) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

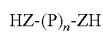

or

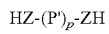

in which Z, P, P', n and p are as defined above.

Examples of compounds containing an amine function that may be mentioned include N-methyldiethanolamine, N-tert-butyldiethanolamine and N-sulphoethyldiethanolamine.

The second compound involved in the preparation of the polyurethane of formula (Ia) is a diisocyanate corresponding to the formula:

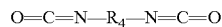

in which $R_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, -hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulphate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulphonated polyesters and sulphonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution. Although the presence of a hydrophilic group Y is optional, cationic associative polyurethanes comprising such a group are, however, preferred.

(II) quaternized cellulose derivatives and polyacrylates containing non-cyclic amino side groups.

The quaternized cellulose derivatives are in particular:

quaternized celluloses modified with groups comprising at least one fatty chain, such as alkyl, arylalkyl or alkylaryl groups comprising at least 8 carbon atoms, or mixtures thereof;

quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$–$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda.

(III) Cationic polyvinyllactams, the family of which was described by the Applicant in French patent application No. 1 101 106.

The said polymers comprise:
a) at least one monomer of vinyllactam or alkyl vinyllactam type;
b) at least one monomer of structure (I) or (II) below:

at least one of the substituents $R_3$, $R_4$, $R_5$ or $R_8$ denotes a linear or branched $C_9$–$C_{30}$ alkyl radical, if m or n is other than zero, then q is equal to 1, if m or n are equal to zero, then p or q is equal to 0.

The cationic poly(vinyllactam) polymers according to the invention may be crosslinked or non-crosslinked, and may also be block polymers.

Preferably, the counterion $Z^-$ of the monomers of formula (I) is selected from the group consisting of halide ions, phosphate ions, the methosulphate ion and the tosylate ion.

Preferably, $R_3$, $R_4$ and $R_5$ denote, independently of each other, a hydrogen atom or a linear or branched $C_1$–$C_{30}$ alkyl radical.

More preferably, the monomer b) is a monomer of formula (I) for which, even more preferably, m and n are equal to zero.

The vinyllactam or alkyl vinyllactam monomer is preferably a compound of structure (IV):

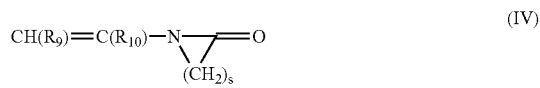

(IV)

in which:
s denotes an integer ranging from 3 to 6,
$R_9$ denotes a hydrogen atom or a $C_1$–$C_5$ alkyl radical,

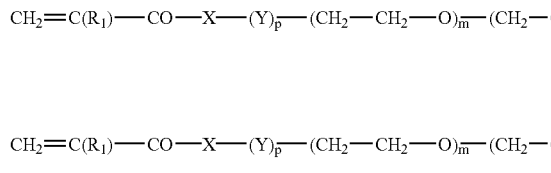

(I)

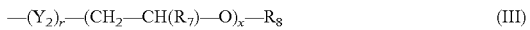

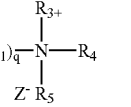

(II)

in which:

X denotes an oxygen atom or a radical $NR_6$, $R_1$ and $R_6$ denote, independently of each other, a hydrogen atom or a linear or branched $C_1$–$C_5$ alkyl radical, $R_2$ denotes a linear or branched $C_1$–$C_4$ alkyl radical, $R_3$, $R_4$ and $R_5$ denote, independently of each other, a hydrogen atom, a linear or branched $C_1$–$C_{30}$ alkyl radical or a radical of formula (III):

—(Y$_2$)$_r$—(CH$_2$—CH(R$_7$)—O)$_x$—R$_8$     (III)

Y, $Y_1$ and $Y_2$ denote, independently of each other, a linear or branched $C_2$–$C_{16}$ alkylene radical, $R_7$ denotes a hydrogen atom, a linear or branched $C_1$–$C_4$ alkyl radical or a linear or branched $C_1$–$C_4$ hydroxyalkyl radical, $R_8$ denotes a hydrogen atom or a linear or branched $C_1$–$C_{30}$ alkyl radical, p, q and r denote, independently of each other, either the value zero or the value 1, m and n denote, independently of each other, an integer ranging from 0 to 100, x denotes an integer ranging from 1 to 100, Z denotes an organic or mineral acid anion, with the proviso that:

$R_{10}$ denotes a hydrogen atom or a $C_1$–$C_5$ alkyl radical, with the proviso that at least one of the radicals $R_9$ and $R_{10}$ denotes a hydrogen atom.

Even more preferably, the monomer (IV) is vinylpyrrolidone.

The cationic poly(vinyllactam) polymers according to the invention may also contain one or more additional monomers, which are preferably cationic or non-ionic.

As compounds that are more particularly preferred according to the invention, mention may be made of the following terpolymers comprising, at least: a)—a monomer of formula (IV), b)—a monomer of formula (I) in which p=1, q=0, $R_3$ and $R_4$ denote, independently of each other, a hydrogen atom or a $C_1$–$C_5$ alkyl radical and $R_5$ denotes a $C_9$–$C_{24}$ alkyl radical, and c)—a monomer of formula (II) in which $R_3$ and R4 denote, independently of each other, a hydrogen atom or a $C_1$–$C_5$ alkyl radical.

Even more preferably, terpolymers comprising, on a weight basis, 40% to 95% of monomer (a), 0.1% to 55% of monomer (c) and 0.25% to 50% of monomer (b) will be used.

Such polymers are described in patent application WO 00/68282, the content of which forms an integral part of the invention.

Cationic poly(vinyllactam) polymers according to the invention that are especially used include vinylpyrrolidone/ dimethylaminopropylmethacrylamide/dodecyldimethyl-methacrylamidopropylammonium tosylate terpolymers, vinylpyrrolidone/dimethylaminopropylmethacrylamide/co-cocoyldimethylmethacrylamidopropylammonim tosylate terpolymers and vinylpyrrolidone/dimethylaminopropyl-methacrylamide/ lauryldimethylmethacrylamidopropylammonium tosylate or chloride terpolymers.

The weight-average molecular mass of the cationic poly (vinyllactam) polymers according to the present invention is preferably between 500 and 20 000 000. It is more particularly between 200 000 and 2 000 000 and even more preferably between 400 000 and 800 000.

Amphoteric Associative Polymers

These are preferably selected from the group consisting of polymers comprising at least one non-cyclic cationic unit. Even more particularly, the ones that are preferred are those prepared from or comprising 1 to 20 mol % of monomer comprising a fatty chain, preferably 1.5 to 15 mol % and even more particularly 1.5 to 6 mol %, relative to the total number of moles of monomers.

The amphoteric associative polymers that are preferred according to the invention comprise, or are prepared by copolymerizing:

1) at least one monomer of formula (Ia) or (Ib):

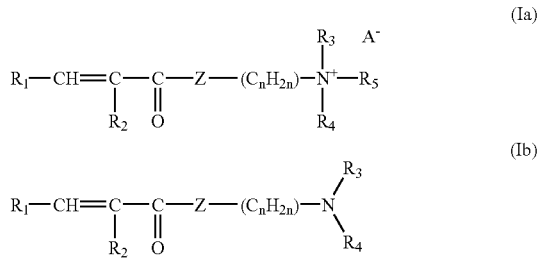

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulphate anion or a halide such as chloride or bromide;

2) at least one monomer of formula (II)

in which $R_6$ and $R_7$, which may be identical or different, represent a hydrogen atom or a methyl radical; and 3) at least one monomer of formula (III):

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) of the present invention are preferably selected from the group consisting of the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$–$C_4$ alkyl halide or a $C_1$–$C_4$ dialkyl sulphate.

More particularly, the monomer of formula (Ia) is selected from the group consisting of acrylamidopropyltrimethylammonium chloride and methacrylamidopropyltrimethy-lammonium chloride.

The monomers of formula (II) of the present invention are preferably selected from the group consisting of the group consisting of acrylic acid, methacrylic acid, crotonic acid and 2-methylcrotonic acid. More particularly, the monomer of formula (II) is acrylic acid.

The monomers of formula (III) of the present invention are preferably selected from the group consisting of the group consisting of $C_{12}$–$C_{22}$ and more particularly $C_{16}$–$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ia), (Ib) or (III)), and preferably from 1.5 mol % to 6 mol %.

The weight-average molecular weights of the amphoteric associative polymers according to the invention may preferably range from 500 to 50 000 000 and are more preferably between 10 000 and 5 000 000.

The amphoteric associative polymers according to the invention may also contain other monomers such as nonionic monomers and in particular such as $C_1$–$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/ (meth)acrylamidopropyltrimethylammonium chloride/ stearyl methacrylate terpolymers.

Associative Polymers of Nonionic Type

According to the invention, these are preferably selected from the group consisting of:

(1) celluloses modified with groups comprising at least one fatty chain; examples that may be mentioned include:

hydroxyethylcelluloses modified with groups comprising at least one fatty chain, such as alkyl, arylalkyl or alkylaryl groups, or mixtures thereof, and in which the alkyl groups are preferably $C_8$–$C_{22}$, for instance the product Natrosol Plus Grade 330 CS® ($C_{16}$ alkyls) sold by the company Aqualon, or the product Bermocoll EHM 100® sold by the company Berol Nobel, those modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

(3) copolymers of vinylpyrrolidone and of fatty-chain hydrophobic monomers; examples that may be mentioned include:
the products Antaron V216® or Ganex V216® (vinylpyrrolidone/hexadecene copolymer) sold by the company I.S.P.
the products Antaron V220® or Ganex V220® (vinylpyrrolidone/eicosene copolymer) sold by the company I.S.P.

(4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1 000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, mention may also be made of Rheolate 205® containing a urea function, sold by the company Rheox, or the Rheolates® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Formum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)].

In one preferred composition according to the present invention, the associative polymers are selected from the group consisting of those of nonionic or cationic type and even more particularly from polyurethane polyethers containing hydrophilic and hydrophobic blocks, polymers with an aminoplast ether skeleton comprising at least one fatty chain, cationic associative polyurethanes, quaternized cellulose derivatives comprising at least one fatty chain, and cationic polyvinyllactams.

In one even more particularly preferred composition according to the invention, the associative polymer is selected from the group consisting of quaternized (C8–C30) alkyl-hydroxyethylcelluloses and especially quaternized laurylhydroxyethylcellulose.

Unsaturated Fatty Alcohols

According to the present invention, these are preferably selected from the group consisting of those whose carbon chain contains from 8 to 30 carbon atoms and preferably from 12 to 22 carbon atoms, and at least one unsaturation and preferably 1 to 3 unsaturations.

Among these, mention may be made especially of linoleyl alcohol, undecylenyl alcohol, palmitoleyl alcohol, linolenyl alcohol, arachidonyl alcohol and erucyl alcohol. Even more particularly, oleyl alcohol is preferably used.

The unsaturated fatty alcohol(s) preferably represent(s) from about 0.5% to 15% and preferably from about 1% to 10% of the total weight of the dye composition, and from about 0.1% to 15% and preferably from about 0.25% to 10% of the total weight of the ready-to-use dye composition (comprising the oxidizing agent).

Oxidation Dyes

The oxidation dyes that may be used according to the invention are preferably selected from the group consisting of oxidation bases and/or couplers.

The compositions according to the invention preferably contain at least one oxidation base.

The oxidation bases that may be used in the context of the present invention include those conventionally used in oxidation dyeing, and among which mention may be made especially of ortho- and para-phenylenediamines, double bases, ortho- and para-aminophenols, the heterocyclic bases below, and also the addition salts thereof with an acid.

Mention may be made especially of:

(I) the para-phenylenediamines of formula (III) below, and the addition salts thereof with an acid:

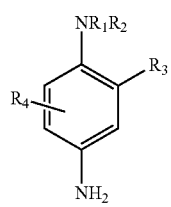

(III)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous, phenyl or 4'-aminophenyl group;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;

$R_1$ and $R_2$ may also form, with the nitrogen atom that bears them, a 5- or 6-membered nitrogen heterocycle optionally substituted with one or more alkyl, hydroxyl or ureido groups;

$R_3$ represents a hydrogen atom, a halogen atom such as a chlorine atom, a $C_1$–$C_4$ alkyl radical, a sulpho radical, a carboxyl radical, a $C_1$–$C_4$ monohydroxyalkyl radical, a $C_1$–$C_4$ hydroxyalkoxy radical, an acetylamino$(C_1$–$C_4)$alkoxy radical, a mesylamino$(C_1$–$C_4)$alkoxy radical or a carbamoylamino$(C_1$–$C_4)$alkoxy radical, $R_4$ represents a hydrogen or halogen atom or a $C_1$–$C_4$ alkyl radical.

Among the nitrogenous groups of formula (III) above, mention may be made especially of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the para-phenylenediamines of formula (III) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(-hydroxyethyl)-para-phenylenediamine, 4-amino-N,N-bis(-hydroxyethyl)-2-methylaniline, 4-amino-N,N-bis(-hydroxyethyl)-2-chloroaniline, 2-hydroxyethyl-para-phenylenediamine, 2-fluoro-para-phenylenediamine, 2-isopropyl-para-phenylenediamine, N-(-hydroxypropyl)-para-phenylenediamine, 2-hydroxymethyl-para-phenylenediamine, N,N-dimethyl-3-methyl-para-phenylenediamine, N-ethyl-N-(-hydroxyethyl)-para-phenylenediamine, N-(,γ-dihydroxypropyl)-para-phenylenediamine, N-(4'-aminophenyl)-para-phenylenediamine, N-phenyl-para-phenylenediamine and 2-hydroxyethyloxy-para-phenylenediamine, 2-acetylaminoethyloxy-para-phenylenediamine, N-(-methoxyethyl)-para-phenylenediamine, 2-methyl-1-N-hydroxyethyl-para-phenylenediamine and N-(4-aminophenyl)-3-hydroxypyrrolidine, and the addition salts thereof with an acid.

Among the para-phenylenediamines of formula (VII) above, para-phenylenediamine, para-tolylenediamine, 2-isopropyl-para-phenylenediamine, 2-hydroxyethyl-para-phenylenediamine, 2-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(-hydroxyethyl)-para-phenylenediamine and 2-chloro-para-phenylenediamine, and the addition salts thereof with an acid, are most particularly preferred.

(II) According to the invention, the term double bases means compounds containing at least two aromatic nuclei bearing amino and/or hydroxyl groups.

Among the double bases that can be used as oxidation bases in the dye compositions in accordance with the invention, mention may be made especially of the compounds corresponding to formula (IV) below, and the addition salts thereof with an acid:

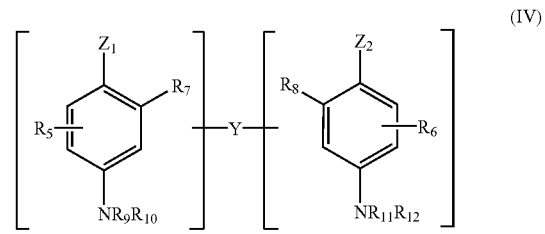

(IV)

in which:

$Z_1$ and $Z_2$, which may be identical or different, represent a hydroxyl or —$NH_2$ radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

it being understood that the compounds of formula (IV) contain only one linker arm Y per molecule.

Among the nitrogenous groups of formula (IV) above, mention may especially be made of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the double bases of formula (IV) above, mention may be made more particularly of N,N'-bis(-hydroxyethyl)-N,N'-bis(4'-aminophenyl)-1,3-diaminopropanol, N,N'-bis(- hydroxyethyl)-N,N'-bis(4'-aminophenyl)ethylenediamine, N,N'-bis(4-aminophenyl)tetramethylenediamine, N,N'-bis(-hydroxyethyl)-N,N'-bis(4-aminophenyl)-tetramethylenediamine, N,N'-bis(4-methylaminophenyl)tetramethylenediamine, N,N'-bis-(ethyl)-N,N'-bis(4'-amino-3'-methylphenyl) ethylenediamine and 1,8-bis(2,5-diaminophenoxy)-3,5-dioxaoctane, and the addition salts thereof with an acid.

Among these double bases of formula (IV), N,N'-bis(-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (V) below, and the addition salts thereof with an acid:

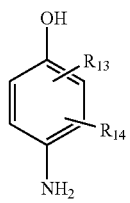

(V)

in which:

$R_{13}$ represents a hydrogen atom, a halogen atom such as fluorine, or a $C_1$–$C_4$ alkyl, $C_1$–$C_4$ monohydroxyalkyl, ($C_1$–$C_4$)alkoxy($C_1$–$C_4$)alkyl, $C_1$–$C_4$ aminoalkyl or hydroxy ($C_1$–$C_4$)alkylamino($C_1$–$C_4$)alkyl radical, $R_{14}$ represents a hydrogen atom, a halogen atom such as fluorine, or a $C_1$–$C_4$-alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy-($C_1$–$C_4$)alkyl radical.

Among the para-aminophenols of formula (V) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(-hydroxyethylaminomethyl)phenol, and the addition salts thereof with an acid.

(IV) The ortho-aminophenols that can be used as oxidation bases in the context of the present invention are chosen especially from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases that can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl) amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylamino-pyrazolo[1,5-a]pyrimidine and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(-hydroxyethyl)-3-methylpyrazole, 4,5-diamino-1-(-hydroxyethylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

According to the present invention, the oxidation bases preferably represent from 0.0005% to 12% by weight approximately relative to the total weight of the composition not comprising the oxidizing agent, and even more preferably from 0.005% to 8% by weight approximately relative to this weight.

The couplers that may be used in the dye composition according to the invention include those conventionally used in oxidation dye compositions, preferably meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

These couplers are chosen more particularly from 2,4-diamino-1-(-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-β-hydroxyethylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

When they are present, these couplers preferably represent from 0.0001% to 10% by weight approximately relative to the total weight of the composition not comprising the oxidizing agent, and even more preferably from 0.005% to 5% by weight approximately.

In general, the addition salts with an acid of the oxidation bases and couplers are chosen especially from the hydrochlorides, hydrobromides, sulphates, tartrates, lactates and acetates.

The dye composition in accordance with the invention may also comprise one or more direct dyes, especially to modify the shades or to enrich them with glints. These direct dyes may especially be selected from the group consisting of neutral, cationic or anionic nitro dyes, azo dyes or anthraquinone dyes, conventionally used or those described especially in patent applications FR-2 782 450, 2 782 451, 2 782 452 and EP-1 025 834, in a weight proportion from about 0.001% to 20% and preferably from 0.01% to 10% of the total weight of the composition.

The ready-to-use composition according to the invention may also comprise in the dye composition and/or the oxidizing composition agents for adjusting the rheology, such as fatty acid amides optionally oxyethylenated (coconut monoethanolamide or diethanolamide, oxyethylenated carboxylic acid alkyl ether monoethanolamide), cellulose thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), crosslinked homopolymers of acrylic acid or of acrylamidopropanesulphonic acid.

The dye composition in accordance with the invention may also comprise one or more direct dyes, especially to modify the shades or to enrich them with glints. These direct dyes may especially be selected from the group consisting of neutral, cationic or anionic nitro dyes, azo dyes or anthraquinone dyes, conventionally used or those described especially in patent applications FR-2 782 450, 2 782 451, 2 782 452 and EP-1 025 834, in a weight proportion from about 0.001% to 20% and preferably from 0.01% to 10% of the total weight of the composition.

The ready-to-use composition according to the invention may also comprise in the dye composition and/or the oxidizing composition at least one cationic or amphoteric polymer.

Cationic Polymers

For the purposes of the present invention, the term "cationic polymer" denotes any polymer containing cationic groups and/or groups that may be ionized into cationic groups.

The cationic polymers that may be used in accordance with the present invention may be selected from the group consisting of all those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are selected from the group consisting of those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type.

These are known products. They are described in particular in French patents Nos 2 505 348 and 2 542 997. Among the said polymers, mention may be made of:

(1) homopolymers or copolymers derived from acrylic or methacrylic esters or amides and comprising at least one of the units of formula (V), (VI), (VII) or (VIII) below:

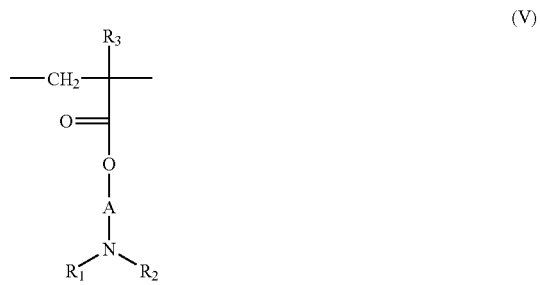

(V)

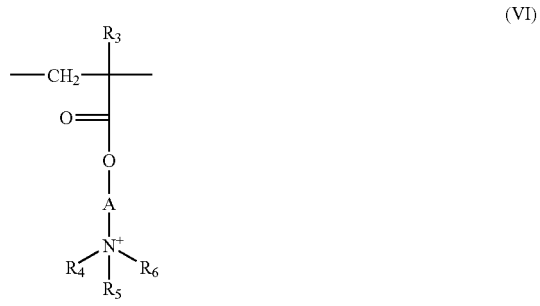

(VI)

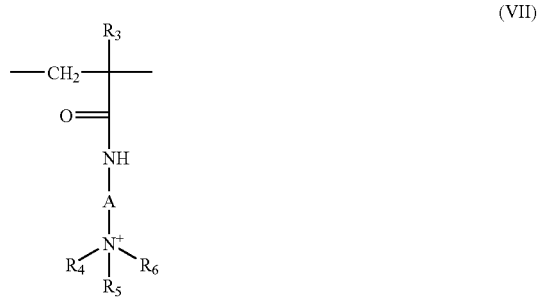

(VII)

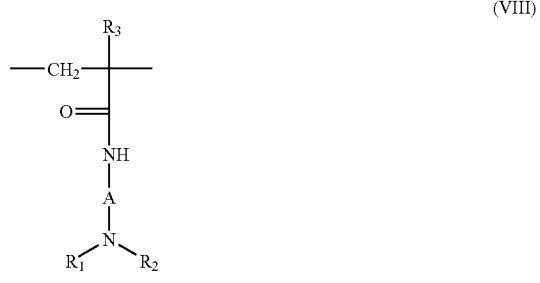

(VIII)

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from an inorganic or organic acid, such as a methosulphate anion or a halide such as chloride or bromide.

The polymers of family (1) can also contain one or more units derived from comonomers which may be selected from the group consisting of the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyl-lactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulphate or with a dimethyl halide, such as the product sold under the name Hercofloc® by the company Hercules, the copolymers of acrylamide and of methacryloyloxyethyltrimethylammonium chloride described, for example, in patent application EP-A-080 976 and sold under the name Bina Quat P 100® by the company Ciba Geigy, the copolymer of acrylamide and of methacryloyloxyethyltrimethylammonium methosulphate sold under the name Reten® by the company Hercules, quaternized or non-quaternized vinylpyrrolidone/dialkylaminoalkyl acrylate or methacrylate copolymers, such as the products sold under the name "Gafquat®" by the company ISP, such as, for example, "Gafquat® 734" or "Gafquat® 755", or alternatively the products known as "Copolymer® 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold in particular under the name Styleze® CC 10 by ISP, and quaternized vinylpyrrolidone/dimethylaminopropylmethacrylamide copolymers such as the product sold under the name "Gafquat® HS 100" by the company ISP.

(2) The cellulose ether derivatives containing quaternary ammonium groups, described in French patent 1 492 597, and in particular polymers sold under the names "JR®" (JR 400, JR 125 and JR 30M) or "LR®" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat® L 200" and "Celquat® H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar® C13 S, Jaguar® C 15, Jaguar® C 17 or Jaguar® C162 by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine® F, F4 or F8" by the company Sandoz.

(8) The polymers obtained by reaction of a polyalkylene polyamine containing two primary amine groups and at least one secondary amine group with a dicarboxylic acid selected from the group consisting of diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett® 57" by the company Hercules Inc. or alternatively under the name "PD 170®" or "Delsette® 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (IX) or (X):

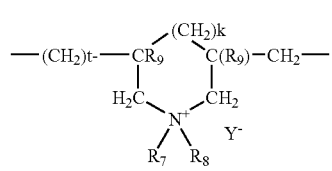

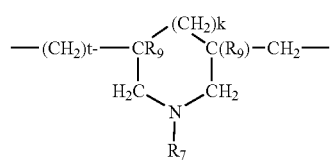

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 6 carbon atoms, a hydroxyalkyl group in which the alkyl group preferably has 1 to 5 carbon atoms, a lower $C_1$–$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; $Y^-$ is an anion such as bromide, chloride, acetate, borate, citrate, tartrate, bisulphate, bisulphite, sulphate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat® 100" by the company Calgon (and its homologues of low weight-average molecular mass) and the copolymers of diallyldimethylammonium chloride and of acrylamide, sold under the name "Merquat® 550".

(10) The quaternary diammonium polymer containing repeating units corresponding to the formula:

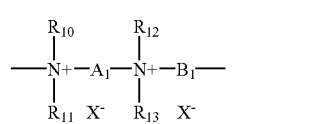

in which formula (XI):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O-Z-O—, where Z denotes a linear or branched hydrocarbon-based radical or a group corresponding to one of the following formulae:

—$(CH_2$—$CH_2$—$O)_x$—$CH_2$—$CH_2$—

—$[CH_2$—$CH(CH_3)$—$O]_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

—$CH_2$—$CH_2$—S—S—$CH_2$—$CH_2$—;

d) a ureylene group of formula: —NH—CO—NH—.

Preferably, $X^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (XII):

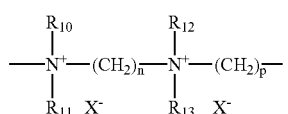

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from an inorganic or organic acid.

(11) Polyquaternary ammonium polymers consisting of repeating units of formula (XIII):

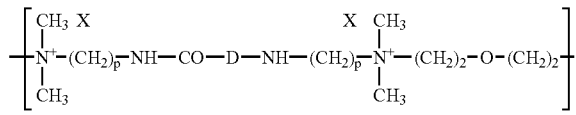

in which p denotes an integer ranging from 1 to 6 approximately, D may be nothing or may represent a group —(CH$_2$)$_r$—CO— in which r denotes a number equal to 4 or 7, X$^-$ is an anion.

Such polymers may be prepared according to the processes described in U.S. Pat. Nos. 4,157,388, 4,702,906 and 4,719,282. They are described in particular in patent application EP-A-122 324.

Among these products, mention may be made, for example, of "Mirapol® A 15", "Mirapol® AD1", "Mirapol® AZ1" and "Mirapol® 175" sold by the company Miranol.

(12) Quaternary polymers of vinylpyrrolidone and of vinylimidazole, such as, for example, the products sold under the names Luviquat® FC 905, FC 550 and FC 370 by the company BASF.

(13) Polyamines such as Polyquart® H sold by Henkel, which is given under the reference name "Polyethylene glycol (15) tallow polyamine" in the CTFA dictionary.

(14) Crosslinked methacryloyloxy(C$_1$–C$_4$)alkyltri (C$_1$–C$_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (1), (9), (10), (11), (12) and (14) and even more preferably the polymers consisting of repeating units of formulae (W) and (U) below:

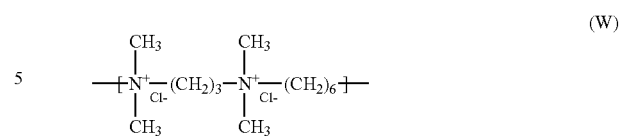

and in particular those whose molecular weight, determined by gel permeation chromatography, is between 9500 and 9900;

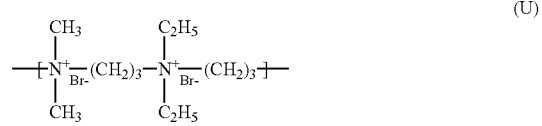

and in particular those whose molecular weight, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers that may be used in accordance with the present invention may be selected from the group consisting of polymers comprising units K and M randomly distributed in the polymer chain, in which K denotes a unit derived from a monomer comprising at least one basic nitrogen atom and M denotes a unit derived from an acidic monomer comprising one or more carboxylic or sulphonic groups, or alternatively K and M may denote groups derived from zwitterionic carboxybetaine or sulphobetaine monomers;

K and M may also denote a cationic polymer chain comprising primary, secondary, tertiary or quaternary amine groups, in which at least one of the amine groups bears a carboxylic or sulphonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are selected from the group consisting of the following polymers:

(1) polymers resulting from the copolymerization of a monomer derived from a vinyl compound bearing a carboxylic group such as, more particularly, acrylic acid, methacrylic acid, maleic acid, -chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537.

Mention may also be made of the sodium acrylate/acrylamidopropyltrimethylammonium chloride copolymer sold under the name Polyquart® KE 3033 by the company Henkel.

The vinyl compound may also be a dialkyldiallylammonium salt such as dimethyldiallylammonium chloride. The copolymers of acrylic acid and of the latter monomer are sold under the names Merquat® 280, Merquat® 295 and Merquat® Plus 3330 by the company Calgon.

(2) Polymers containing units derived from:

a) at least one monomer selected from the group consisting of acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer® or Lovocryl® 47 by the company National Starch are particularly used.

(3) Crosslinked and alkylated polyamino amides partially or totally derived from polyamino amides of general formula:

(XIV)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of the said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

(XV)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XV) above in which x=2 and p=1 and which is derived from ethylenediamine, or the radical derived from piperazine:

c) in proportions of from 0 to 20 mol %, the —NH—$(CH_2)_6$—NH— radical derived from hexamethylenediamine, these polyamino amines being crosslinked by addition of a difunctional crosslinking agent selected from the group consisting of epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably selected from the group consisting of acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) Polymers containing zwitterionic units of formula:

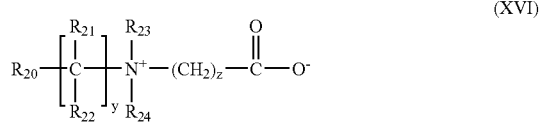

(XVI)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio ethyl methacrylate such as the product sold under the name Diaformer® Z301 by the company Sandoz.

(5) Polymers derived from chitosan containing monomer units corresponding to formulae (XVII), (XVIII) and (XIX) below:

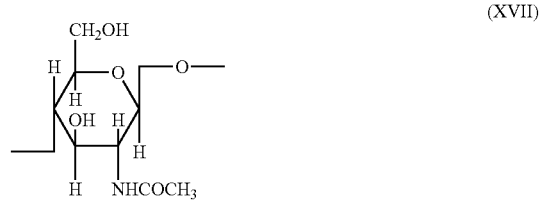

(XVII)

(XVIII)

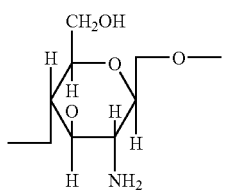

(XIX)

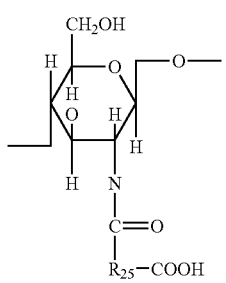

the unit (XVII) being present in proportions of between 0 and 30%, the unit (XVIII) in proportions of between 5 and 50% and the unit (XIX) in proportions of between 30 and 90%, it being understood that, in this unit (XIX), $R_{25}$ represents a radical of formula:

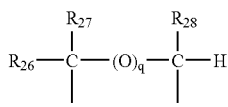

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan®" by the company Jan Dekker.

(7) Polymers corresponding to the general formula (XX) as described, for example, in French patent 1 400 366:

(XX)

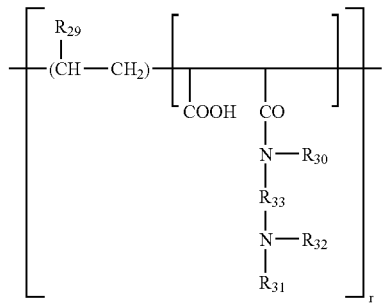

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a —$CH_2$—$CH_2$—, —$CH_2$—$CH_2$—$CH_2$— or —$CH_2$—$CH(CH_3)$— group, $R_{31}$ having the meanings mentioned above, as well as the higher homologues of these radicals and containing up to 6 carbon atoms, r is such that the molecular weight is between 500 and 6 000 000 and preferably between 1000 and 1 000 000.

(8) Amphoteric polymers of the type -D-X-D-X- selected from the group consisting of:

a) polymers obtained by the action of chloroacetic acid or sodium chloroacetate on compounds containing at least one unit of formula:

-D-X-D-X-D- (XXI)

where D denotes a radical

and X denotes the symbol E or E', E or E', which may be identical or different, denotes a divalent radical which is an alkylene radical with a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

-D-X-D-X (XXII)

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylamino-propylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) may represent from 0.01% to 10% by weight, preferably from 0.05% to 5% by weight and even more preferably from 0.1% to 3% by weight relative to the total weight of the composition.

Medium

The medium, for the dye composition, which is suitable for dyeing is preferably an aqueous medium consisting of water possibly advantageously comprising cosmetically acceptable organic solvents including, more particularly, alcohols or diols such as ethyl alcohol, isopropyl alcohol, hexyleneglycol (2-methyl 2,4-pentanediol), neopentyl glycol, 3-methyl -1,5-pentanediol, benzyl alcohol and phenylethyl alcohol, or glycols or glycol ethers such as, for example, ethylene glycol monomethyl, monoethyl and monobutyl ether, propylene glycol or its ethers such as, for example, propylene glycol monomethyl ether, butylene glycol, dipropylene glycol, and also diethylene glycol alkyl ethers such as, for example, diethylene glycol monoethyl ether or monobutyl ether. The solvents may then be present, each in concentrations of between about 0.5% and 20% and preferably between about 2% and 10% by weight, relative to the total weight of the composition.

The dye composition according to the invention may also comprise other surfactants and more particularly oxyethylenated or glycerolated nonionic surfactants that are well known to those skilled in the art in the field under consideration in a proportion ranging from approximately 2 to 40% with respect to the total weight of the composition.

According to the Invention, it is Preferable to Use:

1) fatty alcohols containing from 8 to 22 carbon atoms and oxyethylenated with 1 to 10 mol of ethylene oxide (1 to 10 EO). Among them, there may be mentioned more particularly lauryl alcohol 2 EO, lauryl alcohol 3 EO, decyl alcohol 3 EO and decyl alcohol 5 EO.

2) mono- or polyglycerolated fatty alcohols which may be represented by the formula (II) RO—[CH2—CH(CH$_2$OH)—O]$_m$-H in which R represents a saturated or unsaturated, linear or branched radical containing from 8 to 40 carbon atoms and preferably from 10 to 30 carbon atoms; m represents a number ranging from 1 to 30 and preferably from 1 to 10. Among the mono- or polyglycerolated fatty alcohols that it is more particularly preferred to use are the $C_8$/$C_{10}$ alcohol containing 1 mole of glycerol, the $C_{10}$/$C_{12}$ alcohol containing 1 mol of glycerol and the $C_{12}$ alcohol containing 1.5 mol of glycerol.

Other Adjuvants

The dye composition according to the invention may also contain an effective amount of other agents, known previously elsewhere in oxidation dyeing, such as various common adjuvants, for instance sequestering agents such as EDTA and etidronic acid, UV screening agents, waxes, volatile or non-volatile, cyclic or linear or branched silicones, which are optionally organomodified (in particular with amine groups), preserving agents, ceramides, pseudoceramides, plant, mineral or synthetic oils, vitamins or provitamins, for instance panthenol, opacifiers, etc.

The said composition may also contain reducing agents or antioxidants. These agents may be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid, and, in this case, they are generally present in amounts ranging from about 0.05% to 3% by weight relative to the total weight of the composition.

Needless to say, a person skilled in the art will take care to select the optional additional compound(s) mentioned above such that the advantageous properties intrinsically associated with the ready-to-use composition according to the invention are not, or are not substantially, adversely affected by the envisaged addition(s).

Oxidizing Agent

In the oxidizing composition, the oxidizing agent is preferably selected from the group consisting of hydrogen peroxide, urea peroxide, alkali metal bromates or ferricyanides, and persalts such as perborates and persulphates. It is particularly preferred to use hydrogen peroxide. This oxidizing agent advantageously consists of an aqueous hydrogen peroxide solution whose titre may range, more particularly, from about 1 to 40 volumes and even more preferably from about 5 to 40 volumes.

Oxidizing agents that may also be used are one or more redox enzymes such as laccases, peroxidases and 2-electron oxidoreductases (such as uricase), where appropriate in the presence of their respective donor or co-factor.

The pH of the ready-to-use composition applied to the keratin fibres [composition resulting from mixing together the dye composition and the oxidizing composition] is generally between 3 and 12, limits included. It is preferably between 8.5 and 11, limits included, and may be adjusted to the desired value using acidifying or basifying agents that are well known in the prior art in the dyeing of keratin fibres.

Among the basifying agents which may be mentioned, for example, are aqueous ammonia, alkali metal carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds of the following formula:

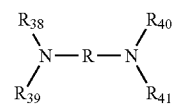

in which R is a propylene residue optionally substituted with a hydroxyl group or a $C_1$–$C_4$ alkyl radical; $R_{38}$, $R_{39}$, $R_{40}$ and $R_{41}$, which may be identical or different, represent a hydrogen atom, a $C_1$–$C_4$ alkyl radical or a $C_1$–$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulphonic acids.

The dyeing process according to the invention preferably consists in applying the ready-to-use composition, prepared extemporaneously at the time of use from the dye composition and the oxidizing composition described above, to wet or dry keratin fibres, and in leaving the composition to act for an exposure time preferably ranging from 1 to 60 minutes approximately, and more preferably from 10 to 45 minutes approximately, in rinsing the fibres and then in optionally washing them with shampoo, then rinsing them again and drying them.

A concrete example illustrating the invention is given below without, however, being limiting in nature.

EXAMPLE 1

The dye composition below was prepared:
Dye Composition:
(expressed as grams of Active Material)

| | |
|---|---|
| Carboxylic lauryl ether acid 4.5 EO (Akypo ® RLM 45 sold by Chem Y) | 7 |
| Lauryl alcohol 2 EO (Dehydol ® LS-2-DEO-N sold by Cognis) | 4 |
| Decyl alcohol 5 EO (Empilan ® KA-5/90-FL sold by Albright & ilson) | 8 |
| Oleyl alcohol | 3 |
| Carboxylic (C13/C15)alkyl ether acid monoethanolamide containing 2 mol of ethylene oxide | 5 |
| Cationic associative polymer (Quatrisoft LM 200 ® sold by Amerchol) | 1 |
| Monoethanolamine | 2 |
| Polyquaternium 6 (Merquat ® 100 sold by Calgon) | 1.5 |
| Ethanol | 11 |
| Propylene glycol | 5 |
| Dipropylene glycol | 5 |
| 1,3-Dihydroxybenzene (resorcinol) | 0.3 |
| para-Phenylenediamine | 0.3 |
| Reducing agents, antioxidants | qs |
| Sequestering agent | qs |
| Fragrance | qs |
| Aqueous ammonia (containing 20.5% ammonia) | 1.6 |
| Demineralized water       qs | 100 |

The dye composition was mixed, at the time of use, in a plastic bowl and for 2 minutes, with an oxidizing composition having an aqueous hydrogen peroxide titre of 20 volumes, at a rate of 1 part of dye composition per 1.5 parts of oxidizing composition.

The mixture obtained was applied to locks of hair containing 90% white hairs and was left to act for 30 minutes.

The locks were then rinsed with water, washed with shampoo, rinsed again with water and then dried and disentangled.

A green-brown shade was thus obtained.

EXAMPLE 2

On a préparé la Composition de teinture suivante:
Composition Colorante:

| (exprimée en grammes de Matière active) | |
|---|---|
| hexylène glycol (2 méthyl-2,4 pentanediol) | 5 |
| dipropylène glycol | 6 |
| acide lauryl éther carboxylique (4.5 OE) | 5.0 |
| amide d'acides de colza oxyéthyléné (4 OE) | 7 |
| Alcool oléique | 4 |
| Alcool laurylique oxyéthyléné (3 OE) | 2 |
| Alcool laurique polyglycérolé (4 moles) | 7 |
| Diuréthane (HMDI) d'alcools (C16/C18) oxyéthylénés (66 OE) et oxypropylénés (14 OP) | 1 |
| Alcool éthylique 96 degrés dénaturé | 9.0 |
| Polycondensat tétraméthyl hexaméthylènediamine/ dichloro 1,3-propylène en solution aqueuse | 2.0 |
| 3-méthyl-1-phényl-5-pyrazolone | 0.15 |
| 1,3-dihydroxybenzène (résorcinol) | 0.0055 |
| 1-hydroxy-3-amino-benzène | 0.03 |
| 1,4-diamino-benzène | 0.4 |
| Acide érythorbique (ou acide d-isoascorbique) | 0.12 |
| Acide éthylène diamine tétracétique | 0.2 |
| Thiolactate d'ammonium en solution aqueuse a 58% (50% en acide thiolactique) | 0.8 |
| Monoéthanolamine pure | 0.7 |
| Parfum | 0.75 |
| Ammoniaque (concentration de référence à 20%) | 8 |
| Eau désionisée | qs 100 |

La composition colorante a été mélangée, au moment de l'emploi, dans un bol en plastique et pendant 2 minutes, à une composition oxydante titrant 20 volumes en eau oxygénée à raison de 1 partie de composition colorante pour 1,5 parties de composition oxydante.

On a appliqué le mélange obtenu sur des mèches de cheveux à 90% de blancs et on a laissé poser 30 minutes.

On a ensuite rincé les mèches à l'eau, on les a lavées an shampooing, à nouveau rincées à l'eau, puis séchées et démêlées.

On a obtenu alors une nuance brun vert.

In view of the above description, one of ordinary skill in the art is able to now make and use a composition comprising at least one oxidation dye, at least one polyoxyalkylenated carboxylic acid ether or a salt thereof, at least one associative polymer and at least one fatty alcohol ($C_8$–$C_{30}$) comprising at least one unsaturation and a ready-to-use composition obtained by mixing such a dye composition and an oxidizing composition comprising at least one oxidizing agent. In addition, one of ordinary skill is now able to make and use a process for dyeing keratin fibres, in particular for human keratin fibres and more particularly the hair, comprising applying to the fibres at least one dye composition comprising, preferably in a medium that is suitable for dyeing, at least one oxidation dye, the colour being developed at alkaline, neutral or acidic pH using an oxidizing composition comprising, preferably in a medium that is suitable for dyeing, at least one oxidizing agent, which is mixed with the dye composition just at the time of use, or which is applied sequentially without intermediate rinsing, the dye composition and the oxidizing composition also comprising, distributed indifferently between the two, at least one polyoxyalkylenated carboxylic acid ether or a salt thereof, at least one associative polymer and at least one fatty alcohol ($C_8$–$C_{30}$) comprising at least one unsaturation as well as a process for dyeing keratin fibres, in particular for human keratin fibres and more particularly the hair, comprising applying to the fibres at least one dye composition comprising, preferably in a medium that is suitable for dyeing, at least one oxidation dye, the colour being developed at alkaline, neutral or acidic pH using an oxidizing composition comprising, preferably in a medium that is suitable for dyeing, at least one oxidizing agent, which is mixed with the dye composition just at the time of use, or which is applied sequentially without intermediate rinsing, the dye composition or the oxidizing composition also comprising, combined in the same composition, at least one polyoxyalkylenated carboxylic acid ether or a salt thereof, at least one associative polymer and at least one fatty alcohol ($C_8$–$C_{30}$) comprising at least one unsaturation. The ordinary artisan is also able to now make and use a multi-compartment device or kit for dyeing human keratin fibres and more particularly the hair, wherein at least one compartment contains a dye composition comprising, preferably in a medium that is suitable for dyeing, at least one oxidation dye, and in that another compartment contains an oxidizing composition comprising, again preferably in a medium that is suitable for dyeing, an oxidizing agent, the dye composition and the oxidizing composition also comprising, distributed indifferently between the two, at least one polyoxyalkylenated carboxylic acid ether or a salt thereof, at least one associative polymer and at least one fatty alcohol ($C_8$–$C_{30}$) comprising at least one unsaturation and a multi-compartment device or kit for dyeing human keratin fibres and more particularly the hair, wherein at least one compartment contains a dye composition comprising, preferably in a medium that is suitable for dyeing, at least one oxidation dye, and in another compartment contains an oxidizing composition comprising, again preferably in a medium that is suitable for dyeing, an oxidizing agent, the dye composition or the oxidizing composition also comprising, combined in the same composition, at least one polyoxyalkylenated carboxylic acid ether or a salt thereof, at least one associative polymer and at least one fatty alcohol ($C_8$–$C_{30}$) comprising at least one unsaturation.

All references, documents, texts, patents, applications, product literature, articles, etc. mentioned above are incorporated by reference herein, as is French patent application 0116740 filed Dec. 21, 2001, priority to which is hereby claimed. Where a numeric range or limit is described herein, all values and subranges falling therewithin are expressly included as if specifically written out.

The invention claimed is:

1. A composition comprising at least one oxidation dye, at least one polyoxyalkylenated carboxylic acid ether or a salt thereof, at least one associative polymer and at least one $C_8$–$C_{30}$ fatty alcohol comprising at least one unsaturation wherein the at least one polyoxyalkylenated carboxylic acid ether or a salt thereof is of formula (I) below:

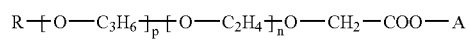

(I)

in which:

R is a ($C_{12}$–$C_{14}$)alkyl; oleyl radical; cetyl radical; stearyl radical or mixture of one or more of the oleyl, cetyl, and stearyl radicals; a nonylphenyl radical; or octylphenyl radical, A is a hydrogen or sodium atom, p=0, and n is from 2 to 20.

2. The composition according to claim 1, wherein, in formula (I), R denotes a ($C_{12}$)alkyl radical, A denotes a hydrogen or sodium atom, p=0 and n ranges from 2 to 10.

3. The composition according to claim 1, wherein the at least one associative polymer is selected from the group consisting of a nonionic polymer and a cationic polymer.

4. The composition according to claim 3, comprising a nonionic polymer selected from the group consisting of polyurethane polyethers containing hydrophilic and hydrophobic blocks, and polymers with an aminoplast ether skeleton comprising at least one fatty chain.

5. The composition according to claim 3, comprising a cationic polymer selected from the group consisting of cationic associative polyurethanes, quaternized cellulose derivatives comprising at least one fatty chain, and cationic polyvinyllactams.

6. The composition according to claim 5, comprising a quaternized cellulose derivative comprising at least one fatty chain selected from the group consisting of quaternized C8–C30 alkylhydroxyethylcelluloses.

7. The composition according to claim 6, comprising quaternized laurylhydroxyethylcellulose.

8. The composition according to claim 1, wherein the $C_8$–$C_{30}$ fatty alcohol comprising at least one unsaturation is selected from the group consisting of ($C_{12}$–$C_{22}$) alcohols comprising from 1 to 3 unsaturations.

9. The composition according to claim 7, comprising oleyl alcohol.

10. The composition according to claim 1, wherein the at least one polyoxyalkylenated carboxylic acid ether or salt thereof represent 2% to 15% by weight relative to the total weight of the composition.

11. The composition according to claim 1, wherein the associative polymer represents 0.01% to 10% by weight relative to the total weight of the composition.

12. The composition according to claim 1, wherein the $C_8$–$C_{30}$ fatty alcohol comprising at least one unsaturation represents 0.5% to 15% by weight relative to the total weight of the composition.

13. The composition according to claim 1, wherein the oxidation dye is selected from the group consisting of oxidation bases and couplers.

14. The composition according to claim 13, further comprising at least one oxidation base.

15. The composition according to claim 14, wherein the oxidation base is selected from the group consisting of ortho- or para-phenylenediamines, double bases, ortho- or para-aminophenols, heterocyclic bases, and the addition salts of these compounds with an acid.

16. The composition according to claim 15, comprising a para-phenylenediamine selected from the group consisting of the compounds of formula (III) below:

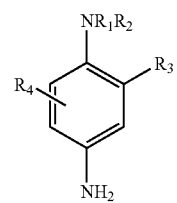

(III)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous, phenyl or 4'-aminophenyl group;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;

$R_1$ and $R_2$ may also form, with the nitrogen atom that bears them, a 5- or 6-membered nitrogen heterocycle optionally substituted with one or more alkyl, hydroxyl or ureido groups;

$R_3$ represents a hydrogen atom, a halogen atom, a $C_1$–$C_4$ alkyl radical, a sulpho radical, a carboxyl radical, a $C_1$–$C_4$ monohydroxyalkyl radical, a $C_1$–$C_4$ hydroxyalkoxy radical, an acetylamino$(C_1$–$C_4)$alkoxy radical, a mesylamino$(C_1$–$C_4)$alkoxy radical or a carbamoylamino$(C_1$–$C_4)$alkoxy radical, $R_4$ represents a hydrogen or halogen atom or a $C_1$–$C_4$ alkyl radical.

17. The composition according to claim 15, comprising a double base selected from the group consisting of compounds of structure (IV) below:

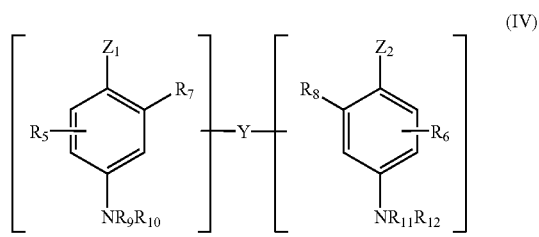

in which:

$Z_1$ and $Z_2$, which may be identical or different, represent a hydroxyl or —$NH_2$ radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;

$R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

wherein the compounds of formula (IV) contain only one linker arm Y per molecule.

18. The composition according to claim 16, wherein the nitrogenous group is selected from the group consisting of amino, mono$(C_1$–$C_4)$ alkylamino, di$(C_1$–$C_4)$alkylamino, tri$(C_1$–$C_4)$alkylamino, monohydroxy$(C_1$–$C_4)$alkylamino, imidazolinium and ammonium radicals.

19. The composition according to claim 15, comprising a para-aminophenol selected from the group consisting of compounds of structure (V) below:

in which:

$R_{13}$ represents a hydrogen atom, a halogen atom, or a $C_1$–$C_4$ alkyl, $C_1$–$C_4$ monohydroxyalkyl, $(C_1$–$C_4)$alkoxy$(C_1$–$C_4)$alkyl, $C_1$–$C_4$ aminoalkyl or hydroxy$(C_1$–$C_4)$ alkylamino$(C_1$–$C_4)$alkyl radical, $R_{14}$ represents a hydrogen atom, a halogen atom, or a $C_1$–$C_4$-alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy$(C_1$–$C_4)$alkyl radical.

20. The composition according to claim 15, comprising a heterocyclic base selected from the group consisting of pyridines, pyrimidines, and pyrazoles.

21. The composition according to claim 14, wherein the oxidation base is present in a concentration ranging from 0.0005% to 12% by weight relative to the total weight of the composition.

22. The composition according to claim 13, comprising a coupler selected from the group consisting of meta-phenylenediamines, meta-aminophenols, meta-diphenols, heterocyclic couplers, and the addition salts of these compounds with an acid.

23. The composition according to claim 13, comprising a coupler in a concentration ranging from 0.0001% to 10% by weight relative to the total weight of the composition.

24. The composition according to claim 15, wherein the addition salts with an acid of the oxidation bases are selected from the group consisting of hydrochlorides, hydrobromides, sulphates, tartrates, lactates and acetates.

25. The composition according to claim 1, further comprising a direct dye.

26. The composition according to claim 1, further comprising at least one reducing agent, in amounts ranging from 0.05% to 3% by weight relative to the total weight of the composition.

27. The composition according to claim 1, further comprising at least one oxyethylenated or glycerolated nonionic surfactant in an amount ranging from 2% to 40% relative to the total weight of the composition.

28. The composition according to claim 1, further comprising at least one cationic or amphoteric polymer in a proportion ranging from 0.01% to 10% relative to the total weight of the composition.

29. A ready-to-use composition obtained by mixing a dye composition as defined in claim 1 and an oxidizing composition comprising at least one oxidizing agent.

30. The composition according to claim 29, wherein the oxidizing agent is selected from the group consisting of hydrogen peroxide, urea peroxide, alkali metal bromates or ferricyanides, persalts, redox enzymes, peroxidases and 2-electron oxidoreductases.

31. The composition according to claim 30, wherein the oxidizing agent is hydrogen peroxide.

32. The composition according to claim 31, wherein the oxidizing agent is an aqueous hydrogen peroxide solution whose titre ranges from 1 to 40 volumes.

33. The composition according to claim 1, having a pH ranging from 3 to 12.

34. The composition according to claim 29, wherein the at least one oxyalkylenated carboxylic acid ether or salt thereof are present in from 0.5% to 15% by weight relative to the total weight of the composition.

35. The composition according to claim 29, wherein the at least one associative polymer is present in 0.0025% to 10% by weight relative to the total weight of the composition.

36. The composition according to claim 29, wherein the $C_8$–$C_{30}$ fatty alcohol comprising at least one unsaturation are present in 0.1% to 15% by weight relative to the total weight of the composition.

37. A process for dyeing keratin fibres comprising applying to the fibres at least one dye composition comprising at least one oxidation dye, the colour being developed at alkaline, neutral or acidic pH using an oxidizing composition comprising at least one oxidizing agent, which is mixed with the dye composition just at the time of use, or which is applied sequentially without intermediate rinsing, the dye composition and the oxidizing composition also comprising, distributed in any manner between the two, at least one polyoxyalkylenated carboxylic acid ether or a salt thereof, at least one associative polymer and at least one $C_8$–$C_{30}$ fatty alcohol comprising at least one unsaturation wherein the polyoxyalkylenated carboxylic acid ether or a salt thereof are of formula (I) below:

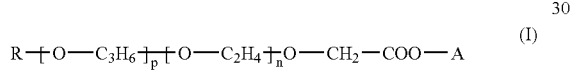

in which:
R is a ($C_{12}$–$C_{14}$)alkyl; oleyl radical; cetyl radical; stearyl radical or mixture of one or more of the oleyl, cetyl, and stearyl radicals; a nonylphenyl radical; or octylphenyl radical,
A is a hydrogen or sodium atom,
p=0, and
n is from 2 to 20.

38. The process for dyeing keratin fibres as claimed in claim 37, comprising, combined in the same composition, at least one polyoxyalkylenated carboxylic acid ether or a salt thereof, at least one associative polymer and at least one $C_8$–$C_{30}$ fatty alcohol comprising at least one unsaturation.

39. The process according to claim 38, comprising applying a composition, prepared extemporaneously at the time of use from the dye composition and the oxidizing composition, to wet or dry keratin fibres, leaving the composition to act for an exposure time ranging from 1 to 60 minutes, rinsing the fibres and then in optionally washing them with shampoo, rinsing them again and drying them.

40. A multi-compartment device or kit for dyeing human keratin fibres, wherein at least one compartment contains a dye composition comprising, at least one oxidation dye, and in that another compartment contains an oxidizing composition comprising an oxidizing agent, the dye composition and the oxidizing composition also comprising, distributed in any manner between the two, at least one polyoxyalkylenated carboxylic acid ether or a salt thereof, at least one $C_8$–$C_{30}$ associative polymer and at least one fatty alcohol comprising at least one unsaturation wherein the polyoxyalkylenated carboxylic acid ether or a salt thereof are of formula (I) below:

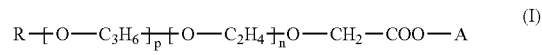

in which:
R is a ($C_{12}$–$C_{14}$)alkyl; oleyl radical; cetyl radical; stearyl radical or mixture of one or more of the oleyl, cetyl, and stearyl radicals; a nonylphenyl radical; or octylphenyl radical,
A is a hydrogen or sodium atom,
p=0, and
n is from 2 to 20.

41. The multi-compartment device or kit according to claim 40, wherein the at least one polyoxyalkylenated carboxylic acid ether or a salt thereof, at least one associative polymer and at least one $C_8$–$C_{30}$ fatty alcohol comprising at least one unsaturation are combined in the same composition.

* * * * *

UNITED STATES PATENT AND TRADEMARK OFFICE
CERTIFICATE OF CORRECTION

| | |
|---|---|
| PATENT NO. | : 7,223,294 B2 |
| APPLICATION NO. | : 10/323770 |
| DATED | : May 29, 2007 |
| INVENTOR(S) | : Patricia Desenne et al. |

Page 1 of 1

It is certified that error appears in the above-identified patent and that said Letters Patent is hereby corrected as shown below:

Column 41, line 12, "are" should read --is--.

Signed and Sealed this

Twentieth Day of November, 2007

JON W. DUDAS
*Director of the United States Patent and Trademark Office*